United States Patent [19]

Raab et al.

[11] Patent Number: 4,754,082

[45] Date of Patent: Jun. 28, 1988

[54] PROCESS FOR THE PREPARATION OF PERFLUOROALKYLALKENOLS

[75] Inventors: Klaus Raab, Burgkirchen; Johanna Pöschl, Halsbach, both of Fed. Rep. of Germany

[73] Assignee: Hoechst Aktiengesellschaft, Frankfurt am Main, Fed. Rep. of Germany

[21] Appl. No.: 69,297

[22] Filed: Jul. 2, 1987

[30] Foreign Application Priority Data

Jul. 4, 1986 [DE] Fed. Rep. of Germany ....... 3622533

[51] Int. Cl.$^4$ ............................................... C07C 33/42
[52] U.S. Cl. .................................... 568/843; 568/677; 568/842; 568/844
[58] Field of Search ......................................... 568/843

[56] References Cited

U.S. PATENT DOCUMENTS 3,285,975  11/1966  Ahlbrecht .

FOREIGN PATENT DOCUMENTS 1101049  1/1968  United Kingdom .

OTHER PUBLICATIONS

Derwent Abstract of Japanese Published App. No. 52-144610 (=JP No. 76-060449, published Dec. 2, 1977) (Daikin Industries KK).

*Primary Examiner*—Howard T. Mars

[57] ABSTRACT

In a novel process for the preparation of perfluoroalkylalkenols, perfluoroalkylhalohydrins are dehydrohalogenated using specific ionic bases, namely using an alkali metal carbonate, an alkali metal hydrogen carbonate or an alkylammonium hydrogen carbonate, in the presence of aprotic and polar solvents. Using this process, high yields of the intended perfluoroalkylalkenols are achieved and only very small amounts, if any at all, of undesired byproducts, such as partially fluorinated ether alcohols and/or partially fluorinated epoxides, are formed.

9 Claims, No Drawings

PROCESS FOR THE PREPARATION OF PERFLUOROALKYLALKENOLS

The invention relates to a process for the preparation of perfluoroalkylalkenols of the formula I below $$R_F\text{—CH}=\text{CH—}(CH_2)_n\text{—OH}$$

in which $R_F$ is a perfluoroalkyl radical having 1 to 18 carbon atoms, and n is an integer from 1 to 6, by reacting a perfluoroalkylhalohydrin of the formula II below $$R_F\text{—CH}_2\text{—CH(Hal)—}(CH_2)_n\text{—OH}$$

in which $R_F$ and n have the abovementioned meaning and Hal represents a halogen, with ionic bases in the presence of a solvent.

Such a process has been disclosed by U.S. Pat. No. 3,285,975 and by British Pat. No. 1,101,049. The bases employed for the reaction (dehydrohalogenation) of the perfluoroalkylhalohydrin are KOH, NaOH or alkali metal alcoholates, such as sodium methylate and potassium ethylate, and the solvents are methanol, ethanol or mixtures of these alcohols with water. This process has the disadvantage that it produces the intended perfluoroalkylalkenols in a relatively low yield. In addition, the reaction proceeds with formation of more or less large amounts of undesired byproducts, such as partly fluorinated ether alcohols of the formula $R_F\text{—CH}_2\text{—CH(OH)—CH}_2\text{—OCH}_3$ and/or partly fluorinated epoxides of the formula

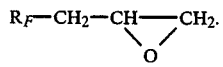

Japanese Preliminary Published Application No. 52-144,610 (Derwent Abstract 05434 A) discloses a process for the preparation of perfluoroalkylpropenol (this compound arises if n is 1 in the formula I mentioned), in which process a perfluoroalkyliodopropanol (this compound arises when Hal is I in the formula II mentioned) is reacted with a specific tertiary amine in the presence of a solvent having a low dielectric constant, such as diethyl ether, dimethyl glycol, dioxane, tetrahydrofuran, methyl acetate and/or methyl ethyl ketone (these are aprotic solvents), or in the presence of a solvent having a high dielectric constant, such as methanol, ethanol, dimethylformamide and/or dimethyl sulfoxide. The particular disadvantage of this process is that it is based on a specific tertiary amine as the second reaction component. In addition, the above mentioned, undesired byproducts, in particular partly fluorinated epoxides, namely perfluoroalkyl-1,2-epoxypropanes, are also formed in this process; this formation occurs above all when the solvents having a high electric constant are employed.

Accordingly, the invention has the object of improving the process mentioned initially for the preparation of perfluoroalkylalkenols where simple basic compounds (ionic bases) are employed as the second reaction component, to the effect that the intended alkenols are obtained in high yield and no significant amount of the byproducts mentioned, or other byproducts, is produced in the reaction.

The process, according to the invention, for the preparation of perfluoroalkylalkenols of the formula I below $$R_F\text{—CH}=\text{CH—}(CH_2)_n\text{—OH}$$

in which $R_F$ is a perfluoroalkyl radical having 1 to 18 carbon atoms, and n is an integer from 1 to 6, by reacting (dehydrohalogenating) a perfluoroalkylhalohydrin of the formula II below $$R_F\text{—CH}_2\text{—CH(Hal)—}(CH_2)_n\text{—OH}$$

in which $R_F$ and n have the meaning mentioned and Hal represents a halogen, with ionic bases in the presence of a solvent, has the characterizing feature that the perfluoroalkylhalohydrin is reacted with an alkali metal carbonate in the molar ratio 1:0.5 to 1.5 or with an alkali metal hydrogen carbonate or an alkylammonium hydrogen carbonate in the molar ratio 1:1.01 to 2 in the presence of a aprotic and polar solvent until no further significant amount of carbon dioxide is produced, and the intended perfluoroalkylalkenol compound is isolated from the reaction product, with the proviso that, when using an alkali metal carbonate and an alkali metal hydrogen carbonate, the reaction is carried out at a temperature from 80° to 150° C. and, when using an alkylammonium hydrogen carbonate, the reaction is carried out at a temperature from −5° to 90° C.

According to the invention, the perfluoroalkylhalohydrin and the alkali metal carbonate are employed in the molar ratio 1:0.5 to 1.5, preferably 1:0.6 to 1. The perfluoroalkylhalohydrin and the alkali metal hydrogen carbonate, and also the alkylammonium hydrogen carbonate, are employed in the molar ratio 1:1.01 to 2, preferably 1:1.1 to 1.5.

When using an alkali metal carbonate and when using an alkali metal hydrogen carbonate, the reaction according to the invention, that is the dehydrohalogenation of the perfluoroalkylhalohydrin, is carried out at a temperature from 80° to 150° C., preferably 90° to 130° C. When using an alkylammonium hydrogen carbonate as the dehydrohalogenating agent, the reaction is carried out at a temperature from −5° to 90° C. As a result of the carbonates and hydrogen carbonates employed, carbon dioxide is produced in the reaction according to the invention. The end of the reaction is indicated by the reduction and cessation of carbon dioxide formation. The reaction time for the reaction according to the invention is generally 5 to 20 hours.

As has been found, the reaction of a perfluoroalkylhalohydrin and an alkylammonium hydrogen carbonate proceeds particularly advantageously with respect to a high yield of the intended compound if a reaction temperature is maintained which is specifically matched to the perfluoroalkylhalohydrin employed. Thus, in the case of a perfluoroalkylhalohydrin of the abovementioned formula II where n=1 (this is a 3-perfluoroalkyl-2-halopropan-1-ol), it is particularly advantageous for a temperature of −5° to 25° C., preferably 0° to 20° C., to be maintained initially until the perfluoroalkylhalopropanol is essentially consumed, and then for a temperature of 40° to 90° C., preferably 50° to 70° C., to be maintained until a significant amount of carbon dioxide is no longer produced. In this reaction procedure, which is two-stage with respect to temperature, a cyclic carbonate is produced in the first stage as an intermediate and is converted in the second stage, i.e. at an elevated reaction temperature, in the presence of alkylammonium hydrogen carbonate which is still present (a catalytic amount is sufficient) into the intended perfluoroalkylpropenol; the yield of perfluoroalkylpropenol is particularly large. If the reaction is carried out from the beginning at the higher temperature, i.e. does not proceed via the intermediate, undesired epoxide is formed besides perfluoroalkylpropenol. The reaction equations below are intended to illustrate the two-stage reaction ($R_F$ and Hal have the abovementioned meaning):

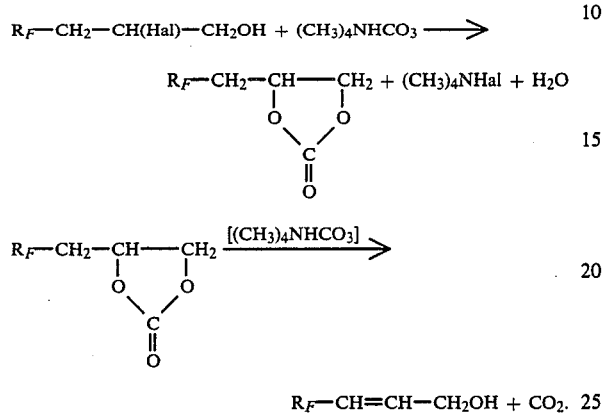

$$R_F—CH=CH—CH_2OH + CO_2.$$

The polyfluorinated, cyclic carbonates obtained at the low temperature specified are not isolated within the scope of the present invention, but are converted into the intended 3-perfluoroalkyl-2-propen-1-ol by heating to the higher temperature specified and by the alkylammonium hydrogen carbonate still present in the reaction mixture (catalytic amounts are sufficient).

In the case of the reaction of an alkylammonium hydrogen carbonate and a perfluoroalkylhalohydrin of the formula mentioned initially, where n is 2 to 6, it is advantageous for a reaction temperature of 40° to 90° C., preferably 50° to 70° C., to be maintained. As in the reactions of a perfluoroalkylhalohydrin with an alkali metal carbonate and an alkali metal hydrogen carbonate, it is not necessary here to conduct the reaction via intermediates in order to achieve a very high yield of the intended perfluoroalkylalkenol; the comparatively low temperature of 40° to 90° C., preferably 50° to 70° C., results from the alkylammonium hydrogen carbonates being more reactive than alkali metal carbonates and alkali metal hydrogen carbonates.

The perfluoroalkyl radical $R_F$ in the formulae I and II is an unbranched or branched alkyl radical, preferably an unbranched alkyl radical, having 1 to 18 carbon atoms, preferably 2 to 10 carbon atoms. Perfluoroalkyl can also be a mixture of perfluoroalkyl groups. n is an integer from 1 to 6, preferably 1 to 2, in particular 1. In the formulae I and II, Hal represents halogen, preferably bromine or iodine. Examples of $R_F$ radicals are $CF_3—$, $CF_3—CF_2—$, $(CF_3)_2CF—$, $CF_3—(CF_2)_3—$, $CF_3—(CF_2)_n—$, in which n is 5, 6, 7, 8, 9, 11, 13 or 15, $(CF_3)_2CF—(CF_2)_2—$, $(CF_3CF_2CF_2)(CF_3)_2C—$, $(CF_3)_2CF—(CF_2)_4—$; $HCF_2—CF_2—$ and $HCF_2—(CF_2)_3—$.

The perfluoroalkylhalohydrins to be employed according to the invention have long been known. The alkali metal carbonates and alkali metal hydrogen carbonates to be employed according to the invention are preferably the sodium and potassium compounds. The alkyl radical in the alkylammonium hydrogen carbonates to be employed according to the invention is preferably a $C_1—$ to $C_4$-alkyl group and in particular methyl or ethyl. Of the alkylammonium hydrogen carbonates, the tetraalkylammonium hydrogen carbonates are preferred.

The reaction according to the invention is carried out in the presence of an aprotic and polar solvent. Suitable such solvents are dimethylformamide, dimethylacetamide, N-methylpyrrolidone, dimethyl sulfoxide, sulfolane, tetramethylurea and acetonitrile, dimethylformamide, dimethylacetamide, N-methylpyrrolidone and acetonitrile being preferred. It has been found that dimethylformamide, dimethylacetamide and N-methylpyrrolidone are particularly suitable solvents when an alkali metal carbonate and an alkali metal hydrogen carbonate are used, and acetonitrile is the particularly suitable solvent when an alkylammonium hydrogen carbonate is used. The amount of solvent in which the perfluoroalkylhalohydrins are essentially soluble and the carbonates and hydrogen carbonates are essentially insoluble can vary within broad limits. For reasons of expediency, sufficient solvent is used so that a readily stirrable suspension of the halohydrin, carbonate or hydrogen carbonate and solvent employed is present. In general, 0.1 to 15 liters, preferably 0.2 to 2 liters, of solvent are employed per mole of perfluoroalkylhalohydrin.

The manner in which the reaction according to the invention is generally carried out is that the starting compounds and the solvent are introduced into a reaction vessel, and the suspension obtained is brought to the reaction temperature with stirring, whereupon the reaction proceeds. In the case of reaction temperatures which are below room temperature, the starting compounds, the solvent and the suspension are correspondingly cooled. The course of the reaction can be followed with reference to the abovementioned evolution of carbon dioxide and/or by NMR spectroscopy.

When the reaction is complete, the intended perfluoroalkylalkenol is preferably isolated by taking up the reaction product in water, an organic phase and an aqueous phase being formed. The organic phase essentially comprises the intended perfluoroalkylalkenol and the aqueous phase essentially comprises water and the water-soluble compounds which are present. After separating off the organic phase, this can be distilled in order to obtain a particularly pure perfluoroalkylalkenol.

The intended perfluoroalkylalkenols are obtained in high yield using the process according to the invention. No significant amounts of undesired byproducts, if any, are produced using this process. The bases, the alkali metal carbonates, the alkali metal hydrogen carbonates and the alkylammonium hydrogen carbonates to be employed according to the invention as the second reaction component, besides the perfluoroalkylhalohydrin, are very simple compounds, which represents a further great advantage of the process according to the invention.

The invention is now illustrated in greater detail with reference to Examples.

EXAMPLE 1

60.8 g ((0.2 mol) of $CF_3CF_2—CH_2—CHI—CH_2OH$, 30 (0.3 mol) of $KHCO_3$ and 200 ml of N-methylpyrrolidone are introduced into a 500 ml three-necked flask fitted with reflux condenser, stirrer and internal thermometer. The suspension is stirred at 100° C. for 14 hours until the evolution of $CO_2$ is complete. After cooling to room temperature, the flask contents are filtered. About 0.5 liter of water is added to the filtrate, and the brown lower liquid phase is separated off in the separating funnel. The N-methylpyrrolidone/water upper phase is extracted repeatedly with diethyl ether. The combined diethyl ether extracts and the brown lower liquid phase are distilled together in a water-pump vacuum after stripping off the diethyl ether. The fraction having the boiling point 39° to 43° C. at 8 mbar comprises colorless, liquid trans—$CF_3CF_2$—CH=CH—$CH_2OH$ and a little cis—$CF_3CF_2$—CH=CH—$CH_2OH$. The yield of trans—$CF_3CF_2$—CH=CH—$CH_2OH$ is 65% of theory by weight, and that of cis—$CF_3CF_2$—CH=CH—$CH_2OH$ is 4% of theory by weight. The compounds were identified by $^1H$, $^{13}C$ and $^{19}F$ NMR spectroscopy.

EXAMPLE 2

352.8 g (0.7 mol) of $CF_3(CF_2)_5$—$CH_2$—CHI—$CH_2OH$, 105 g (1.05 mol) of $KHCO_3$ and 1,400 ml of dimethylacetamide are introduced into a 2 liter three-necked flask fitted with reflux condenser, stirrer and internal thermometer. The suspension is stirred at 100° C. for 8 hours until the evolution of $CO_2$ is complete. After cooling to room temperature, the precipitated KI and the excess $KHCO_3$ are filtered off. About 2 liters of water are added to the filtrate, and the brown lower liquid phase is separated off in a separating funnel. The lower phase is washed by shaking ten times with 200 ml of water in each case in order to remove the dimethylacetamide, and is then distilled via a split-tube column under a water-pump vacuum. The fraction having the boiling point 85° to 88° C. at 9 to 10 mbar comprises colorless, liquid trans—$CF_3(CF_2)_5$—CH=CH—$CH_2OH$ and a little cis—$CF_3(CF_2)_5$—CH=CH—$CH_2OH$. The yield of trans—$CF_3(CF_2)_5$—CH=CH—$CH_2OH$ is 85% of theory by weight, and that of cis—$CF_3(CF_2)_5$—CH=CH—$CH_2OH$ is 6% of theory by weight. The compounds were identified by $^1H$, $^{13}C$ and $^{19}F$ NMR spectroscopy.

EXAMPLE 3

Example 2 is repeated with the following changes: 600 ml of dimethylformamide are employed in place of 1,400 ml of dimethylacetamide, and the mixture is stirred for 10 hours at 100° C. instead of for 8 hours at 100° C. The yield of trans—$CF_3(CF_2)_5$—CH=CH—$CH_2OH$ is 75% of theory by weight, and that of cis—$CF_3(CF_2)_5$—CH=CH—$CH_2OH$ is 5% of theory by weight.

EXAMPLE 4

Example 2 is repeated with the following changes: 700 ml of N-methylpyrrolidone are employed in place of 1,400 ml of dimethylacetamide, and the mixture is stirred for 10 hours at 100° C. instead for 8 hours at 100° C. The yield of trans—$CF_3(CF_2)_5$—CH=CH—$CH_2OH$ is 77% of theory by weight, and that of cis—$CF_3(CF_2)_5$—CH=CH—$CH_2OH$ is 5% of theory by weight. In addition, due to the relatively short reaction time, 5% by weight of the solid carbonate of the formula

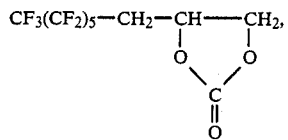

which would be converted into the desired compound with a longer reaction time, are still present in the distillation residue.

EXAMPLE 5

50.4 g (0.1 mol) of $CF_3(CF_2)_5$—$CH_2$—CHI—$CH_2OH$, 16.2 g (0.12 mol) of $N(CH_3)_4HCO_3$ and 300 ml of acetonitrile are introduced into a 500 ml three-necked flask fitted with reflux condenser, stirrer and internal thermometer. The suspension is stirred for 6 hours at 15° to 20° C. and then for 5 hours at 65° C. After filtration, the majority of the acetonitrile is stripped off, and water is added to the liquid residue. The brown lower liquid phase is separated off in a separating funnel and distilled in a water-pump vacuum. The yield of trans—$CF_3(CF_2)_5$—CH=CH—$CH_2OH$ is 78% of theory by weight, and that of cis-$CF_3(CF_2)_5$—CH=CH—$CH_2OH$ is 2% of theory by weight. In addition, about 1% of theory by weight of epoxide of the formula

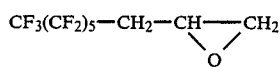

is produced as an undesired byproduct.

EXAMPLE 6

100.8 g (0.2 mol) of $CF_3(CF_2)_5$—$CH_2$—CHI—$CH_2OH$, 15.9 g (0.15 mol) of $Na_2CO_3$ and 300 ml of dimethylacetamide are introduced into a 500 ml three-necked flask fitted with reflux condenser, stirrer and internal thermometer. The suspension is stirred for 12 hours at 110° C. until the evolution of $CO_2$ is complete. After cooling to room temperature, about 0.5 liter of water is added to the flask contents. The brown lower liquid phase is washed by shaking about ten times with water and distilled in a water-pump vacuum. The yield of trans—$CF_3(CF_2)_5$—CH=CH—$CH_2OH$ is 77% of theory by weight, and that of cis-$CF_3(CF_2)_5$—CH=CH—$CH_2OH$ is 6% of theory by weight.

EXAMPLE 7

Example 6 is repeated with the following change: 20.7 g (0.15 mol) of $K_2CO_3$ are employed in place of 15.9 g of $Na_2CO_3$. The yield of trans—$CF_3(CF_2)_5$—CH=CH—$CH_2OH$ is 82% of theory by weight, and that of cis—$CF_3(CF_2)_5$—CH=CH—$CH_2OH$ is 6% of theory by weight.

EXAMPLE 8

100.8 g (0.2 mol) of $CF_3(CF_2)_5$—$CH_2$—$CHI$—$CH_2OH$, 33.6 g (0.4 mol) of $NaHCO_3$ and 300 ml of dimethylacetamide are introduced into a 500 ml three-necked flask fitted with reflux condenser, stirrer and internal thermometer. The suspension is stirred for 10 hours at 125° C. until the evolution of $CO_2$ is complete. Work-up is effected as in Example 6. After distillation, 66% of theory by weight of trans—$CF_3(CF_2)_5$—$CH$=$CH$—$CH_2OH$ and 6% of theory by weight of cis—$CF_3(CF_2)_5$—$CH$=$CH$—$CH_2OH$ are obtained.

EXAMPLE 9

51.8 g (0.1 mol) of $CF_3(CF_2)_5$—$CH_2$—$CHI$—$CH_2OH$, 15 g (0.15 mol) of $KHCO_3$ and 200 ml of dimethylacetamide are introduced into a 500 ml three-necked flask fitted with reflux condenser, stirrer and internal thermometer. The suspension is stirred for 8 hours at 95° to 100° C. until the evolution of $CO_2$ is complete. The flask contents are filtered, and 0.5 liter of water is added to the filtrate. The lower liquid phase is separated off in a separating funnel, washed by stirring several times with water, and subsequently distilled. The colorless liquid distillate, having the boiling point 85° to 88° C. at about 10 mbar, contains trans—$CF_3(CF_2)_5$—$CH$=$CH$—$CH_2$—$CH_2OH$ (yield: 66% of theory by weight), cis—$CF_3(CF_2)_5$—$CH$=$CH$—$CH_2$—$CH_2OH$ (yield: 11% of theory by weight) and trans—$CF_3(CF_2)_5$—$CH_2$—$CH$=$CH$—$CH_2OH$ (yield: 6% of theory by weight).

EXAMPLE 10

436.7 g (0.72 mol) of $CF_3(CF_2)_7$—$CH_2$—$CHI$—$CH_2OH$, 108 g (1.08 mol) of $KHCO_3$ and 550 ml of dimethylacetamide are introduced into a 1 liter three-necked flask fitted with reflux condenser, stirrer and internal thermometer. The suspension is stirred for 14 hours at 100 to 105° C. until the evolution of $CO_2$ is complete. After cooling to room temperature, the KI and unreacted $KHCO_3$ are filtered off. 1 liter of water is added to the filtrate, and the brown lower liquid phase is separated off in a separating funnel. This phase is washed by stirring about ten times with water and then distilled via a split-tube column in a water-pump vacuum. The distillate having the boiling point 102 to 110° C. at 6 to 8 mbar comprises colorless, liquid trans—$CF_3(CF_2)_7$—$CH$=$CH$—$CH_2OH$ and a little cis-$CF_3(CF_2)_7$—$CH$=$CH$—$CH_2OH$. The yield of trans—$CF_3(CF_2)_7$—$CH$=$CH$—$CH_2OH$ is 80% of theory by weight and that of cis-$CF_3(CF_2)_7$—$CH$=$CH$—$CH_2OH$ is 6% of theory by weight.

In the Examples according to the invention, the intended perfluoroalkylalkenols are obtained in high yield. No significant amounts, if any, of undesired by-products are produced.

COMPARISON EXAMPLE 1

100.8 g (0.2 mol) of $CF_3(CF_2)_5$—$CH_2$—$CHI$—$CH_2OH$ and 15.7 g (0.28 mol) of KOH in 130 ml of methanol are introduced into a 500 ml three-necked flask fitted with reflux condenser, stirrer and internal thermometer. The mixture is stirred for 9 hours at the reflux temperature (69° C.). About ⅔ of the methanol is then removed by distillation at atmospheric pressure, and water is added to the remaining flask contents. The lower liquid phase is washed with water and distilled. The distillate having the boiling point 79° to 81° C. at 7 mbar comprises trans-$CF_3(CF_2)_5$—$CH$=$CH$—$CH_2OH$ (yield: 34% of theory by weight) and $CF_3(CF_2)_5$—$CH_2$—$CH(OH)$—$CH_2$—$OCH_3$ (yield: 46% of theory by weight).

COMPARISON EXAMPLE 2

100.8 g (0.2 mol) of $CF_3(CF_2)_5$—$CH_2$—$CHI$—$CH_2OH$, 14 g (0.25 mol) of KOH and 300 ml of dimethylacetamide are introduced into a 500 ml three-necked flask fitted with reflux condenser, stirrer and internal thermometer. The flask contents are stirred for 10 hours at 90° to 100° C., and 0.5 liter of water is then added at room temperature. The brown lower phase is washed by stirring several times with water and then distilled. The yield of trans-$CF_3(CF_2)_5$—$CH$=$CH$—$CH_2OH$ is 48% by weight, that of cis-$CF_3(CF_2)_5$—$CH$=$CH$—$CH_2OH$ is 3% by weight and that of

is 3% by weight.

The relatively voluminous distillation residue contains $CF_3(CF_2)_5$—$CH_2$—$CH(OH)$—$CH_2I$, a little $CF_3(CF_2)_5$—$CH_2$—$CH(OH)$—$CH_2OH$ and a little trans-$CF_3(CF_2)_5$—$CH$=$CH$—$CH_2OH$.

In the two comparison examples, the yield of the intended perfluoroalkylpropenol is noticeably lower than in the Examples according to the invention. In addition, a relatively large amount of undesired by-products, such as partially fluorinated ether alcohols (in Comparison Example 1) and partially fluorinated epoxides (in Comparison Example 2), is produced in the comparison examples.

We claim:

1. A process for the preparation of perfluoroalkylalkenols of the formula I below $$R_F\text{—CH}=\text{CH—(CH}_2)_n\text{—OH}$$

in which $R_F$ is a perfluoroalkyl radical having 1 to 18 carbon atoms, and n is an integer from 1 to 6, by reacting a perfluoroalkylhalohydrin of the formula II below $$R_F\text{—CH}_2\text{CH(Hal)—(CH}_2)_n\text{—OH,}$$

in which $R_F$ and n have the abovementioned meaning and Hal represents a halogen, with ionic bases in the presence of a solvent, wherein the perfluoroalkylhalohydrin is reacted with an alkali metal carbonate in the molar ratio 1:0.5 to 1.5 or with an alkali metal hydrogen carbonate or an alkylammonium hydrogen carbonate in the molar ratio 1:1.01 to 2 in the presence of an aprotic and polar solvent, until essentially no more carbon dioxide is produced, and the intended perfluoroalkylalkenol compound is isolated from the reaction product, with the proviso that, when using an alkali metal carbonate and an alkali metal hydrogen carbonate, the reaction is carried out at a temperature from 80° to 150° C. and, when an alkylammonium hydrogen carbonate is used, the reaction is carried out at a temperature from −5° to 90° C.

2. The process as claimed in claim 1, wherein the perfluoroalkylhalohydrin and the alkali metal carbonate are employed in the molar ratio 1:0.6 to 1.

3. The process as claimed in claim 1, wherein the perfluoroalkylhalohydrin, the alkali metal hydrogen carbonate and the alkylammonium hydrogen carbonate are employed in a molar ratio of 1:1.1 to 1.5.

4. The process as claimed in claim 1, wherein, when using an alkali metal carbonate and an alkali metal hydrogen carbonate, the reaction is carried out at a temperature from 90° to 130° C.

5. The process as claimed in claim 1, wherein, when using an alkylammonium hydrogen carbonate, the reaction is carried out at a temperature from −5° to 90° C., a reaction temperature from 40° to 90° C. being maintained in the case of a perfluoroalkylhalohydrin when n=2 to 6, and a reaction temperature from −5° to 25° C. initially being maintained in the case of n=1 until the perfluoroalkylhalohydrin is essentially consumed, and the reaction mixture subsequently being kept at a temperature from 40° to 90° C. until essentially no more carbon dioxide is produced.

6. The process as claimed in claim 1, wherein $R_F$ is a perfluoroalkyl radical having 2 to 10 carbon atoms.

7. The process as claimed in claim 1, wherein n is 1.

8. The process as claimed in claim 1, wherein the solvent employed is dimethylformamide, dimethylacetamide, N-methylpyrrolidone or acetonitrile.

9. The process as claimed in claim 1, wherein the solvent employed is dimethylformamide, dimethylacetamide or N-methylpyrrolidone when an alkali metal carbonate and an alkali metal hydrogen carbonate are used, and is acetonitrile when an alkylammonium hydrogen carbonate is used.

* * * * *